(12) United States Patent
Xu et al.

(10) Patent No.: US 7,497,980 B2
(45) Date of Patent: Mar. 3, 2009

(54) MICRONEEDLES AND MICRONEEDLE FABRICATION

(75) Inventors: Yuan Xu, Singapore (SG); Mei Ma Chen, Singapore (SG); Zhongli Li, Singapore (SG); Chee Yen Lim, Singapore (SG); Pei Ying Joyce Tan, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 451 days.

(21) Appl. No.: 10/505,035

(22) PCT Filed: Nov. 10, 2003

(86) PCT No.: PCT/SG03/00260

§ 371 (c)(1),
(2), (4) Date: Aug. 17, 2004

(87) PCT Pub. No.: WO2005/044364

PCT Pub. Date: May 19, 2005

(65) Prior Publication Data

US 2006/0202385 A1    Sep. 14, 2006

(51) Int. Cl.
*B29C 33/42* (2006.01)
(52) U.S. Cl. .................................... 264/219; 219/69.13
(58) Field of Classification Search ................ 264/129, 264/130, 219, 338; 219/69.12
See application file for complete search history.

(56) References Cited

U.S. PATENT DOCUMENTS

| | | | |
|---|---|---|---|
| 5,658,515 A | 8/1997 | Lee et al. | |
| 6,021,559 A | 2/2000 | Smith | |
| 6,334,856 B1 | 1/2002 | Allen et al. | |
| 6,379,324 B1 | 4/2002 | Gartstein et al. | |
| 6,471,903 B2 * | 10/2002 | Sherman et al. | 264/328.1 |
| 6,511,463 B1 * | 1/2003 | Wood et al. | 604/272 |
| 6,551,849 B1 * | 4/2003 | Kenney | 438/34 |
| 6,627,835 B1 * | 9/2003 | Chung et al. | 219/69.12 |
| 6,749,792 B2 * | 6/2004 | Olson | 264/328.1 |
| 6,899,838 B2 * | 5/2005 | Lastovich | 264/102 |
| 2003/0009113 A1 * | 1/2003 | Olson | 600/573 |
| 2003/0135161 A1 | 7/2003 | Fleming et al. | |

FOREIGN PATENT DOCUMENTS

| | | |
|---|---|---|
| EP | 1 008 642 | 4/2001 |
| EP | 1 287 847 | 5/2003 |
| JP | 2-22602 | 1/1990 |
| WO | 00/74764 | 12/2000 |
| WO | WO 02/064193 A2 | 8/2002 |
| WO | WO 03/024518 A2 | 3/2003 |

OTHER PUBLICATIONS

Notification of Reasons for Refusal from Corresponding Japanese Patent Application No. 2005-510475 mailed on Aug. 26, 2008.

* cited by examiner

*Primary Examiner*—Jill L Heitbrink
(74) *Attorney, Agent, or Firm*—Merchant & Gould P.C.

(57) ABSTRACT

A master mould is made by wire cutting a plate in two or more directions to provide a base with an array of master mould needles protruding therefrom. The size and shape of the master mould needles can readily be varied by varying the angles of upward and downward cuts in the two or more directions. The master mould is used to make a secondary mould by hot embossing a secondary mould plate onto the master mould. This forms through-holes in the secondary mould. The secondary mould is plated with a layer of metal, which forms a microneedle array.

31 Claims, 13 Drawing Sheets

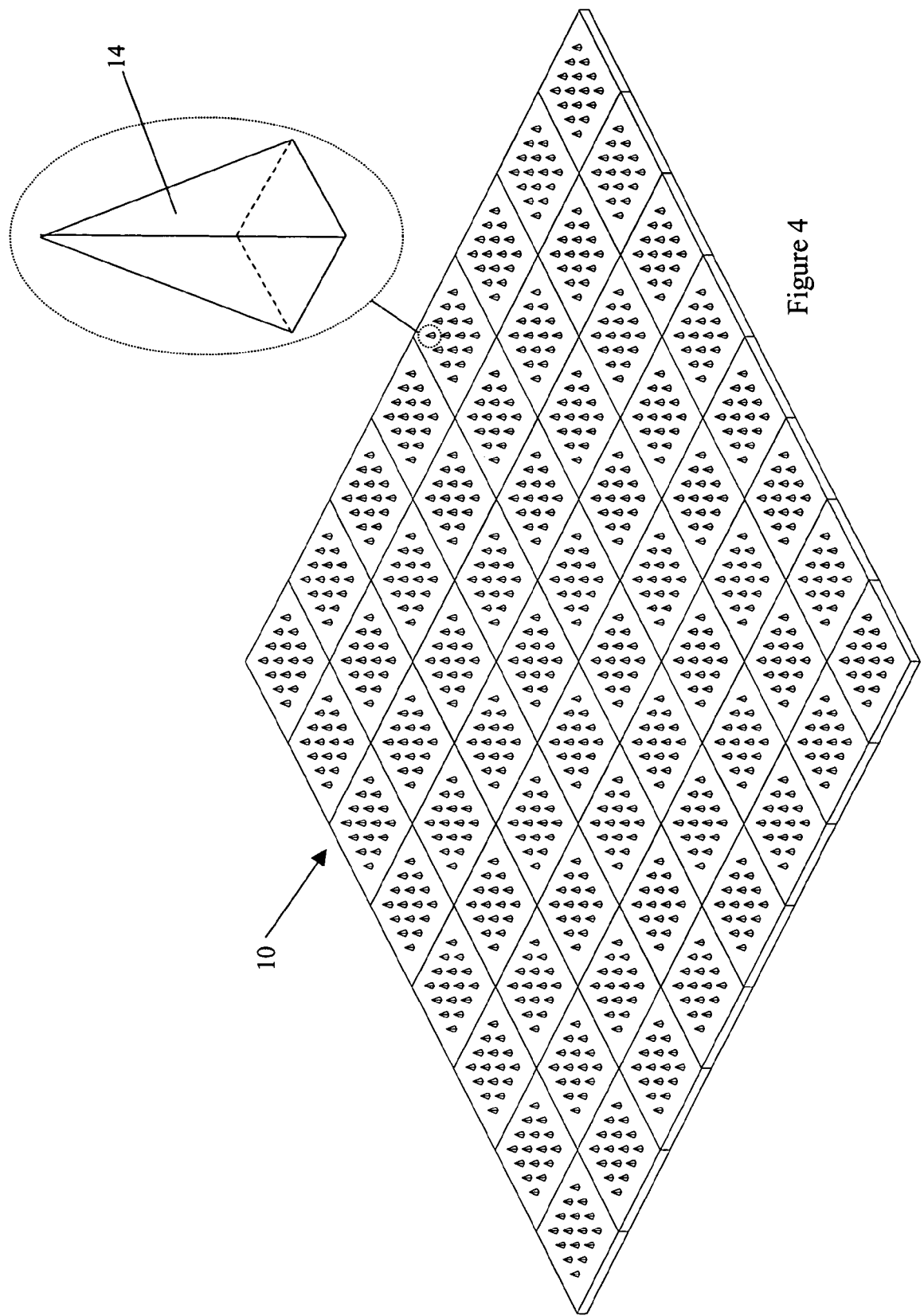

MICRONEEDLES AND MICRONEEDLE FABRICATION

FIELD OF THE INVENTION

The present invention relates to microneedles. In particular it relates to the fabrication of microneedles, for instance in arrays, and to fabricated microneedles.

BACKGROUND TO THE INVENTION

Microneedles are small needles, typically in the range of from 1 μm (micron) to 3 mm long and from 10 nm to 1 mm in diameter at their bases, although the ranges can be wider, for instance up to 10 mm long and 2 mm at their bases. Microneedles typically have applications in biomedical devices, for instance for transdermal drug delivery. Existing microneedle fabrication techniques tend to produce microneedles that are too soft (made of polymeric materials), too brittle (made of silicon) or too costly, or tend to be too unreliable. For transdermal drug delivery applications, where penetration of the outer skin (stratum corneum) is necessary, there are minimum requirements for the strength and ductility of a microneedle. Prices should be low, as microneedles are usually single-use products.

European Patent Application Publication No. EP-A1-1,088,642, published on 4 Apr. 2001 in the name of Becton Dickinson & Co. describes a method of fabricating an array of solid microneedles by moulding. A silicon master mould member with a recessed surface is placed into a mould cavity. A plastic material is pumped into the mould cavity. Microneedles are formed in the recesses in the master mould member.

European Patent Application Publication No. EP-A1-1,287,847, published on 5 Mar. 2003 in the name of Lifescan, Inc. describes a method of fabricating hollow microneedles by plastic injection moulding. The mould is made of two parts. The top part has a conical recess within its moulding surface. One of the top and bottom parts has a protrusion extending to the moulding surface of the other part for forming the needle lumen.

U.S. Pat. No. B1-6,334,856, issued on 1 Jan. 2002 to Allen et al. describes various ways of making arrays of hollow microneedles. In one example masks are formed on the tips of solid microneedles of a silicon microneedle array, a layer of silicon dioxide or metal is coated onto the microneedle array, and the silicon is etched away to leave a hollow microneedle array of metal or silicon dioxide. In another example a layer of epoxy is cast onto an array of solid silicon microneedles. The level of the epoxy is reduced to below the tips of the microneedles. The silicon array is removed, leaving an epoxy secondary mould. A Ti—Cu—Ti seed layer is splutter-deposited onto the epoxy secondary mould and Ni—Fe electroplated onto the seed layer. The epoxy layer is then removed, leaving an array of hollow metal microneedles.

U.S. Pat. No. B1-6,379,324, issued on 30 Apr. 2002 to Gartstein et al. describes various ways of making arrays of hollow microneedles. One way involves self-moulding a polymer film over micro-pillars through heating. A second approach is to place a polymer film over micro-pillars, heat the film and press it down over the micro-pillars using a recessed plate. A third way is to heat a plastic film in the lower part of a mould and to bring the upper part of the mould down onto the lower part. The upper part of the mould has micro-recesses, with micro-pillars protruding from their centres. As the upper part of the mould comes down, the lower parts of the micro-pillars displace the plastic of the plastic film up into the micro-recesses.

SUMMARY OF THE INVENTION

According to one aspect of the invention, there is provided a method of manufacturing a master mould for use in making microneedles, from a block of a first material. The method comprises cutting across the block in at least two different directions to provide a master mould comprising a base surface with a plurality of master mould needles protruding therefrom. The master mould needles correspond to the microneedles to be made.

According to a second aspect of the invention, there is provided a master mould manufactured according to the first aspect.

According to a third aspect of the invention, there is provided a method of manufacturing a secondary mould for use in making microneedles. The method comprises: providing a master mould, forming a secondary mould and removing the secondary mould from the master mould. The master mould is as manufactured according to the second aspect. The secondary mould is formed on the master mould, with through-holes therethrough, the through-holes corresponding to the master mould needles. The through-holes extend from a first surface of the secondary mould, in contact with the master mould base surface during forming of the secondary mould, to an opposing, second surface of the secondary mould.

According to a fourth aspect of the invention, there is provided a mould for a secondary mould. The mould for a secondary mould comprises a master mould as manufactured according to the second aspect. The master mould base surface forms a first surface of the cavity of the mould for a secondary mould. The master mould needles extend into the cavity towards a second, opposing surface of the cavity.

According to a fifth aspect of the invention, there is provided a method of manufacturing a secondary mould for use in making microneedles. The method comprises manufacturing a secondary mould according to the third aspect by injection moulding the secondary mould into the mould for a secondary mould of the fourth aspect.

According to a sixth aspect of the invention, there is provided a secondary mould manufactured according to the third or fifth aspects.

According to a seventh aspect of the invention, there is provided a secondary mould for use in making microneedles. The secondary mould comprises: a plurality of through holes and a plurality of grooves. The plurality of through holes extend through the secondary mould from a first surface to a second, opposing surface. The plurality of grooves extend in the second surface of the secondary mould. The grooves intercept the through holes near the second surface.

According to a eighth aspect of the invention, there is provided a method of manufacturing microneedles. The method comprises: providing a secondary mould, forming a microneedle layer and removing the microneedle layer from the secondary mould. The secondary mould is provided according to the third or fifth aspect or the secondary mould is as defined in the sixth or seventh aspect. The microneedle layer is formed onto a first surface of the secondary mould and within the through-holes of the secondary mould.

According to an ninth aspect of the invention, there is provided a microneedle mould, comprising a secondary mould according to the sixth or seventh aspect, with the first surface of the secondary mould forming a first surface of a microneedle mould cavity and the secondary mould throughholes extending into the first surface of the microneedle mould cavity.

According to an tenth aspect of the invention, there is provided a method of manufacturing microneedles according to the eighth aspect, using the microneedle mould of the ninth aspect.

According to an eleventh aspect of the invention, there is provided one or more microneedles manufactured according to the eighth or tenth aspect.

Thus the invention in one embodiment is able to provide master mould by wire cutting a plate in two or more directions to provide a base with an array of master mould needles protruding therefrom. The size and shape of the master mould needles can readily be varied by varying the angles of upward and downward cuts in the two or more directions. The master mould is used to make a secondary mould by hot embossing a secondary mould plate onto the master mould. This forms through holes in the secondary mould. The secondary mould is plated with a layer of metal, which forms a microneedle array.

INTRODUCTION TO THE DRAWINGS

The invention is now further described by way of non-limitative examples with reference to the accompanying drawings, in which:

FIG. 4 is an isometric view of a master mould with 64 (8×8) mould needle arrays;

DETAILED DESCRIPTION

Figure 1:
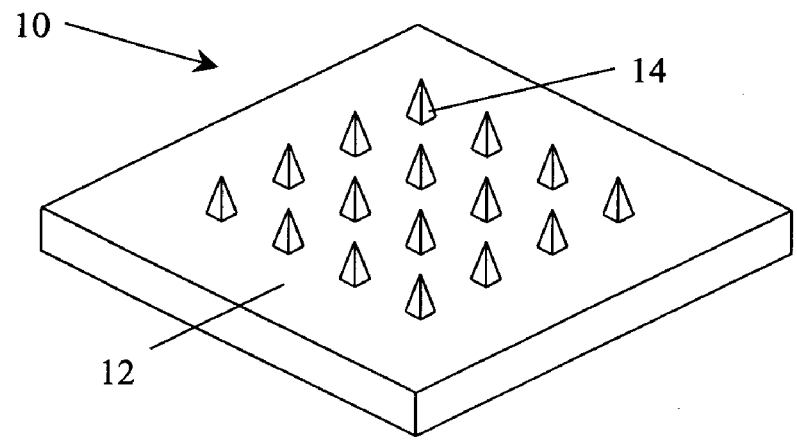
FIG. 1 is a view of a master mould according to an embodiment of the invention.

In the drawings, like numerals on different Figures are used to indicate like elements throughout.

A method of fabricating microneedles as described herein typically involves three main steps:
(i) making a master mould;
(ii) making a secondary mould; and
(iii) forming the microneedles.

(i) Making a Master Mould

A master mould 10 according to a first embodiment of the invention is shown in FIG. 1. The master mould 10 has a generally parallelepiped base 12 from which extend an array of master mould needles 14 from one face. For simplicity only a single master mould needle array is shown in the Figures although fabrication would normally involve an array of many such arrays formed on the master mould and secondary mould and on the product on which the microneedles are formed.

Making the master mould 10 according to this embodiment involves precision machining. A block of material, in this exemplary embodiment in the form of a parallelepiped tool steel plate (for example AISI A2 or another steel alloy designation) is hardened first. Then all the surfaces are mirror finished. After the finishing, one side of the plate is cut by precision wire cutting (or other precision machining, for example CNT machining), as shown with reference to FIGS. 2, 3A and 3B.

Figure 2:
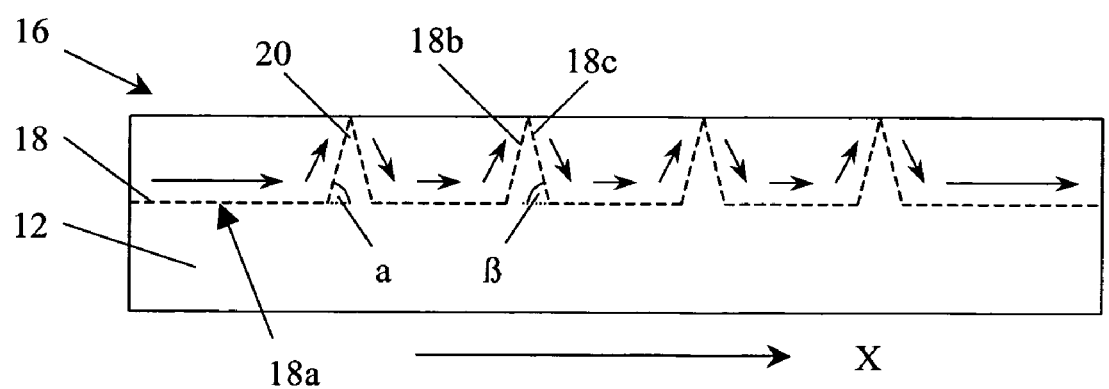
FIG. 2 is a side view of a plate to be cut into the master mould of FIG. 1, showing the path a wire takes during one wire cutting pass.
Figure 3A:
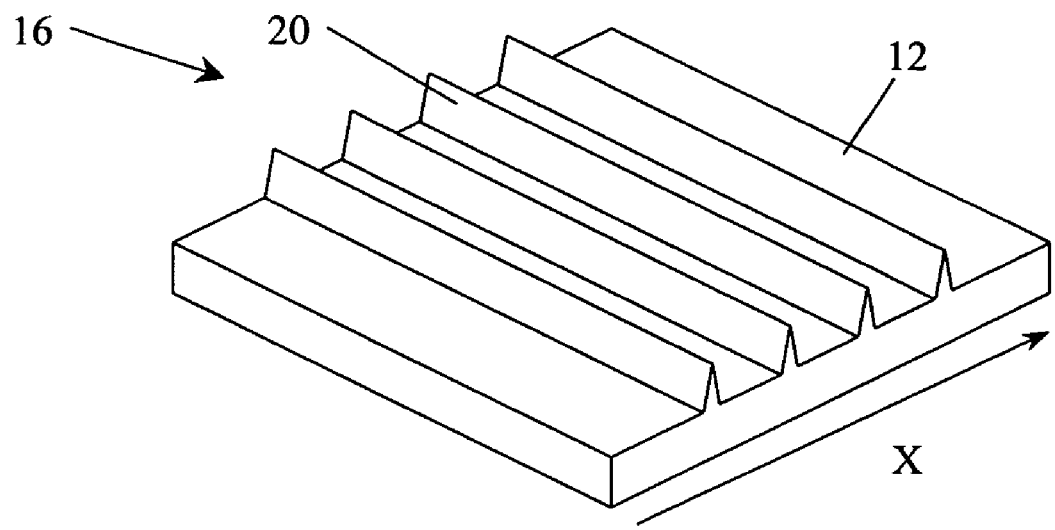
FIGS. 3A and 3B are views of the plate of FIG. 2 at different times during the cutting process.
Figure 3B:
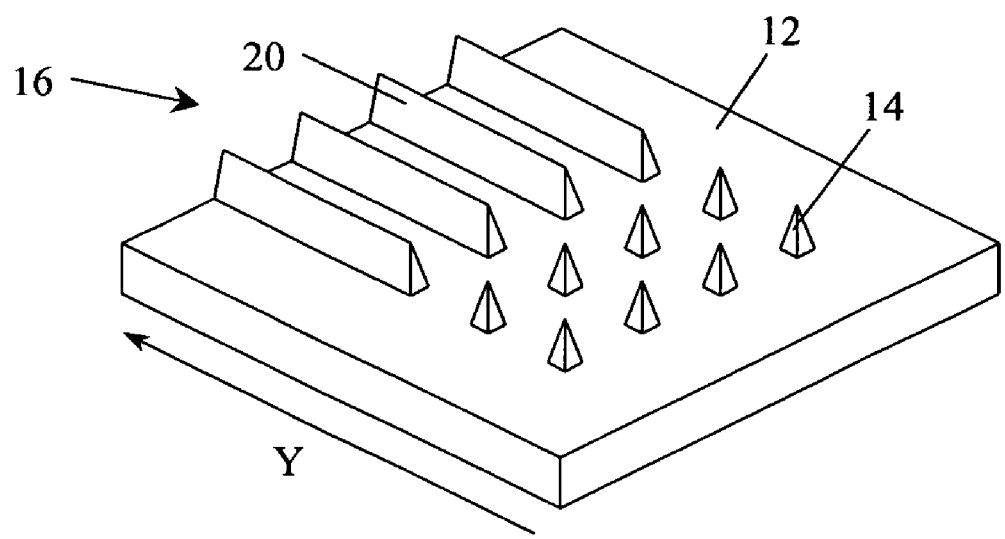

FIG. 2 is a side view of a parallelepiped tool steel plate 16 with mirror finished surfaces, to be cut into the master mould of FIG. 1, showing the path a wire takes during one wire cutting pass. FIGS. 3A and 3B are views of the plate of FIG. 2 at different times during the cutting process. FIG. 3A is an isometric view of the same tool steel plate 16 after one pass, in an X direction. FIG. 3B is an isometric view of the same tool steel plate 16 after one pass, in an X direction and half a pass in a Y direction.

The first pass of the wire cutting is conducted in the X direction. FIG. 2 shows the wire cutting line 18. The wire cutting line 18 extends horizontally through the plate 16, at a base level for a base cutting portion 18a, until the position of the first master mould needle line, at which point the wire cutting line 18 extends upwards along a first sloped cutting portion 18b, at a upward cut angle α, being the angle to the surface of the base 12 at which the first sides of the master mould needles extend. At the top surface of the plate 16, the wire cutting line 18 extends downwards again towards the base level. The wire cutting line 18 extends downwards along a second sloped cutting portion 18c, at a downward cut angle β, being the angle to the surface of the base 12 at which the second sides of the master mould needles, opposing the first sides, extend. In this embodiment the upward and downward cut angles α, β are equal, thus first and second sides of the master mould needles are isosceles. In the first pass, this pair of upward and downward cuts, the first and second sloped cutting portions 18b, 18c, creates a ridge 20 between two base cutting portions 18a. The wire cutting line 18 continues horizontally again along the base level for another base cutting portion 18a to the position of the next master mould needle 14, at which point the wire cutting line 18 extends upwards again and then downwards again, thus cutting another ridge 20. This continues until there are as many ridges 20 as there are to be master mould needles in the X direction.

Ideally at the top of the upward cut, the downward cut begins immediately. However, current wire cutting machines, no matter how accurate they are, always have precision limitations. Thus, when the wire reaches the top of one ridge 20, in practice it must move laterally to some extent (typically 1-20 μm [microns]), before it can go downward. Thus, in practice, the formed ridges 20 and later formed mould needles 14 currently have small flat top surfaces instead of perfect sharp tips. Where the ridges 20 and mould needles 14 appear in the drawings as having perfect sharp tips, instead of small flat tip surfaces, this is for simplicity.

After the first cutting pass, the top part of the plate 16 is removed, leaving parallel ridges on one surface of the steel plate, as appear in FIG. 3A. Then the plate 16 (or the wire cutting tool) is turned 90 degrees around the Z-axis (the direction orthogonally down through the plate 16). A second wire cutting pass in the Y direction is now conducted. This follows the same path as the first pass, as shown in FIG. 2, except that it is now in a direction at 90 degrees to the direction of the first cut. The upward and downward cuts are at third and fourth side angles. As there is already a first cut, the second wire cutting pass produces individual master mould needles 14, instead of cutting a second row of ridges. FIG. 3B shows the plate 16 half way through the second wire cutting pass. Some master mould needles 14 have been produced and the ridges 20 still extend half way along the plate. At the end of the second wire cutting pass, the plate appears as in FIG. 1. In this embodiment, each master mould needle has the same shape of a square pyramid frustum.

FIGS. 1 to 3 show the fabrication process for a master mould having only one master mould needle array. Several tens or even more master mould needle arrays can be formed by two wire cutting passes, when a larger steel plate is used. For example, FIG. 4 is an isometric view of a master mould 10 with 64 (8×8) master mould needle arrays fabricated in two wire cutting passes. A single master mould needle 14 is shown enlarged.

The master mould need not be steel but can be made from another metal/alloy such as an aluminium alloy, zinc alloy, etc. One or more hard coatings, for example, diamond carbon coating, a diamond like carbon coating (DLC), an electroless Ni coating, a hard chrome coating, a nitride coating, a carbide coating or a boride coating may be applied onto the master mould surface and master mould needles. This to increase the hardness of the master mould, to extend the life of the master mould. Additionally or instead there may be added a release layer coating layer, for example an aluminium coating, a titanium coating, a chromium coating, a carbon coating, a diamond like carbon coating or some or appropriate coating to facilitate the release of a plate used in the creation of a secondary mould. Some of the coatings can increase hardness and act as a release layer.

Figure 5:
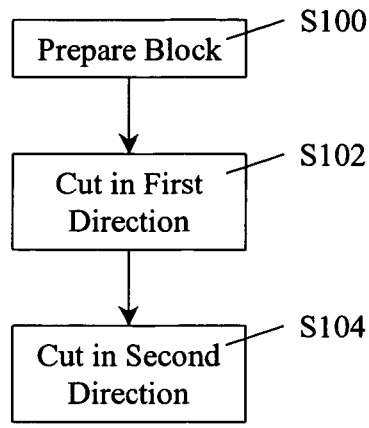
FIG. 5 is a flowchart relating to the manufacture of a master mould according to an exemplary embodiment.

A flowchart describing the steps involved in making the master mould according to this embodiment is shown in FIG. 5. At step S100 a block of material is prepared. The block is cut in a first direction at step S102, to form a plurality of ridges, and in a second direction at step S104, to turn the ridges into master mould needles.

(ii) Making a Secondary Mould

Figure 6A:
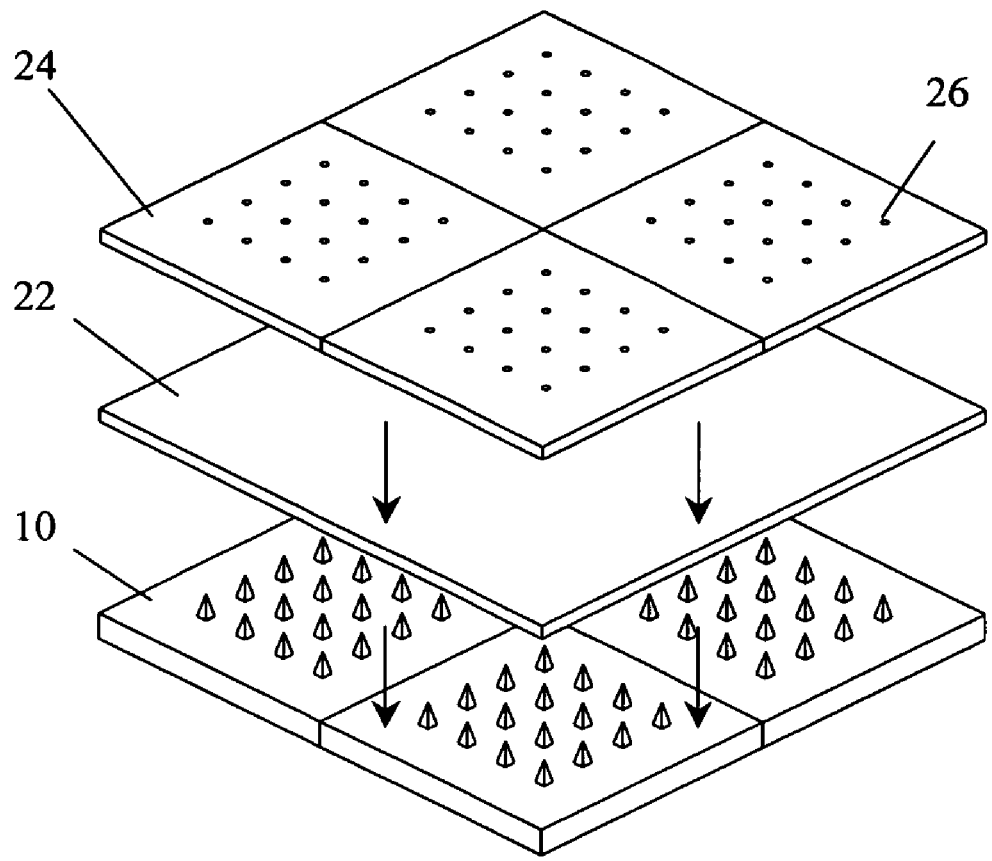
FIGS. 6A and 6B are views of an embossing process for making a secondary mould according to an embodiment of the invention.
Figure 6B:
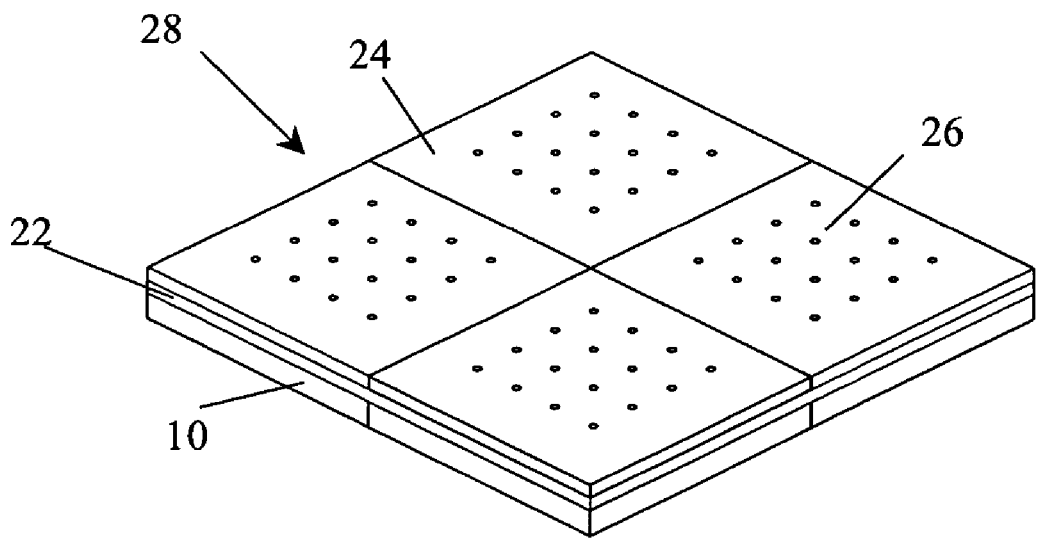

An embossing process for making a secondary mould is shown schematically in FIGS. 6A and 6B, using a master mould 10 for four microneedle arrays as an example.

As appears in FIG. 6A, the master mould 10 is placed horizontally on the bottom surface of a hot press (not shown) with the master mould needles 14 facing upwards. An embossing plate 22 is placed on top of the master mould 10. The embossing plate 22 of this embodiment is made from a thermoplastic polymeric material (such as polycarbonate, nylon polyimide, PMMA, etc.) and is of a thickness equal to the height of the final microneedles that are to be fabricated. The plate thickness is preferably between 50 to 2000 μm (microns) but the range can be larger. A top plate 24 is placed above the embossing plate 22. The top plate 24 has arrays of through-holes 26 that are in alignment with the master mould needle arrays of the master mould 10. The through-holes 26 are cylindrical in shape, each with a cross sectional area large enough to contain the square cross section of the master mould needle 14 penetrating in.

The combined thickness of the embossing plate 22 and the top plate 24 is larger than the height of the master mould needles 14. The height of the master mould needles 14 is greater than that of the final microneedles to facilitate their full penetration through the embossing plate 22.

The holes 26 in the top plate 24 do not need to be through-holes. They could simply be recesses in the underside of the top plate 24 to accommodate the tips of the master mould needles 14 extending above the top surface of the embossing plate 22. Likewise the holes 26 in the top plate 24 do not need to be cylindrical; they could be square, frusto-conical, frusto-pyramidal or any other shape to accommodate the tips of the master mould needles 14 extending above the top surface of the embossing plate 22.

The top plate 24 is made from a material that can sustain a subsequent heating temperature, for instance steel, which may be of the same type as that from which the master mould 10 is made. Alternatively, the top plate 24 is made from other materials, for example aluminium or an aluminium alloy (or some other metal or alloy) or another thermoplastic material with a working temperature higher than that of the material of the embossing plate 22.

The master mould 10 is heated to a first temperature, a little over the softening temperature of the embossing plate 22 (for polycarbonate, it is above 150° C., in the range between 150 and 200° C.). At the first temperature, the top plate 26 is pressed down by the upper plate of the hot press, at the same temperature, forming a sandwich block 28 (of the three layers: the master mould 10, the embossing plate 22 and the top plate 24), as shown in FIG. 6B.

The temperature is allowed to drop to a second value, lower than the softening temperature of the embossing plate 22. At this second temperature value, the embossing plate 22 hardens. Then the top plate 24 is removed and the embossed embossing plate is released from the bottom master mould 10, with square pyramid frustum through-holes 'printed' into it. The embossed embossing plate forms a secondary mould. The master mould 10 and the top plate 24 are reusable for making further secondary moulds.

Figure 7A:
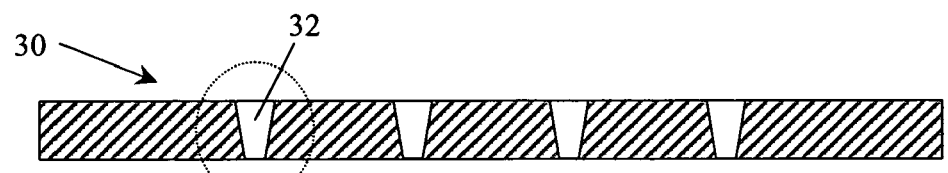
FIG. 7A is a cross section through a portion of a secondary mould.
Figure 7B:
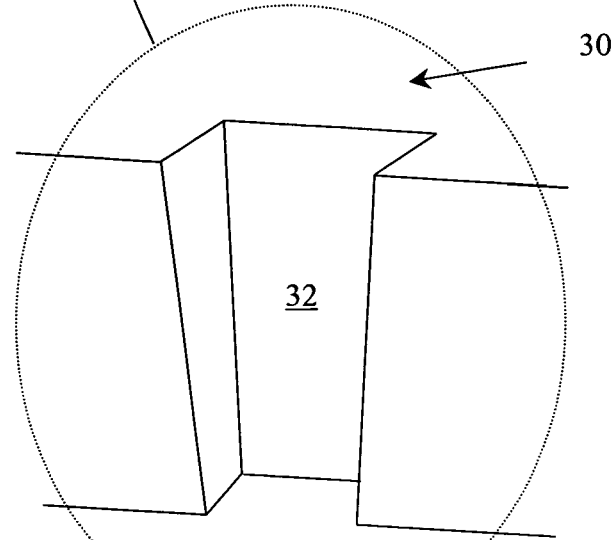
FIG. 7B is an enlarged view of an opening in the secondary mould of FIG. 7A.

FIG. 7A is a cross section through a portion of a secondary mould 30, showing the square pyramid frustum through-holes 32. FIG. 7B is an enlarged isometric view of one such through-hole 32. These Figures are inverted relative to the orientation of FIGS. 6A and 6B.

In another exemplary embodiment, the orientation of the embossing process can be inverted. The master mould can be placed on the top, with the master mould needles facing down, the embossing plate below the master mould and the top (now the bottom) plate at the bottom.

In a further alternative process, another plate is used instead of the top plate, without any openings on it. It is made of the same material as the embossing plate 22 or of a material of the same or a lower softening temperature. A separation film may then be provided between the embossing plate 22 and the new top plate to prevent the two plates bonding together during the hot press (embossing) process. The separation film may be in the form of a Ti, Cr, or Al layer, applied by PVD, CVD, evaporation, etc., or simply a layer of liquid injection mould release agent film.

Figure 8:
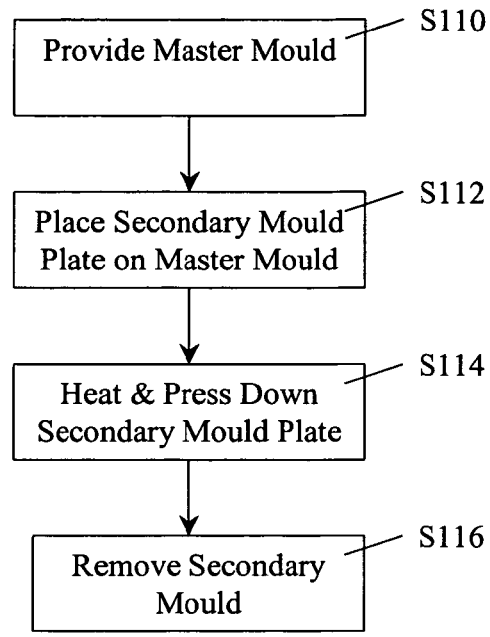
FIG. 8 is a flowchart relating to the manufacture of a secondary mould according to a further exemplary embodiment.

A flowchart describing the steps involved in making the secondary mould according to this embodiment is shown in FIG. 8. At step S110 a master mould is provided. At step S112 a secondary mould plate is placed on top of the master mould. The secondary mould plate is heated and pressed down at step S114 to form through-holes through the secondary mould plate. The secondary mould is removed from the master mould at step S116.

(iii) Forming the Microneedles

The embossing plate 22 embossed during the hot embossing process, with square pyramid frustum through-holes 32 is a secondary mould 30. Microneedle arrays are made using a secondary mould 30, as described with reference to FIGS. 9A and 9B.

Figure 9A:
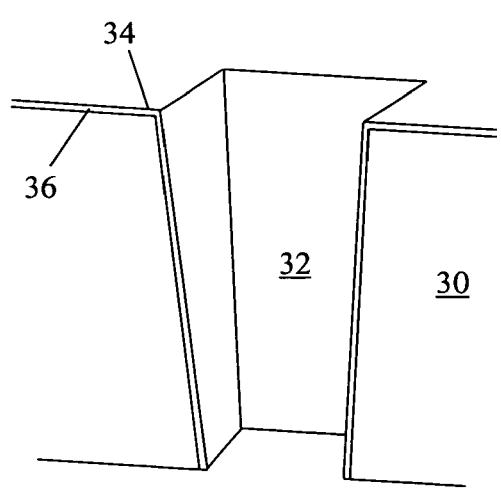
FIGS. 9A and 9B show the use of the secondary mould of FIG. 7A in the manufacture of a microneedle array.

The secondary mould 30 is metallised by depositing a thin conductive seed film 34 (such as Ni, Ti, Cr, Al, Ag or another conductive film) onto a top surface 36 of the secondary mould 30, as shown in FIG. 9A. The top surface 36 of the secondary mould 30 for this purpose is the surface with the larger openings to the pyramid frustum through-holes 32 (it is the bottom surface during the formation of the secondary mould 30 as described earlier with reference to FIGS. 6A and 6B). The method used for depositing the seed film 34 can be PVD, CVD, thermo-evaporation, electroless plating of Ni or another metal, through the silver-mirror reaction (for a thin Ag coat) or some other process. This deposition covers the whole of the top surface 36 as well as lining the through-holes 32. The deposited layer 34 typically has a substantially constant thickness, and is typically within the range of between 10 nm and a few microns (or more).

Figure 9B:
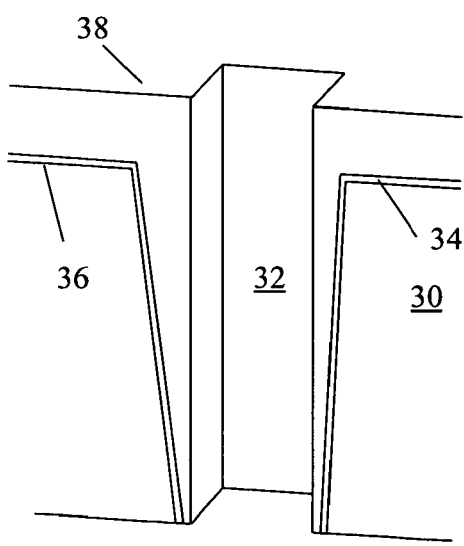

Electroforming of Ni or Ni/Fe alloy or another metal/alloy is then conducted to provide the microneedle layer 38. The microneedle layer 38 is on top of the thin metal seed film 34 on the secondary mould 30 and in the through-holes 32, as shown in FIG. 9B. The thickness of the plated metal/alloy preferably ranges from 20-100 μm (microns) (although wider ranges are also possible). Other techniques can be used instead of electroforming, for instance electroless plating or vapour deposition, particularly for depositing non-metal layers, such as carbon, although these may be expensive.

Figure 10A:
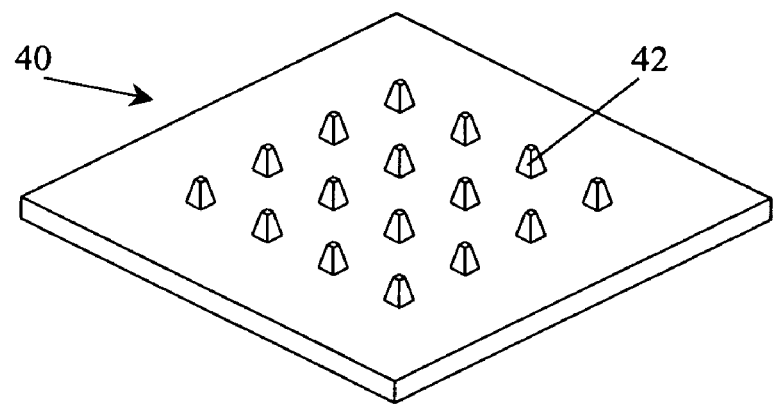
FIG. 10A is an isometric view of e microneedle array fabricated using the secondary mould of FIG. 7A.
Figure 10B:
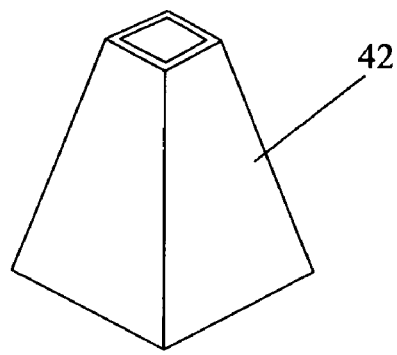
FIG. 10B is an enlarged view of a microneedle of the array of FIG. 10A.

The plated metal/alloy structure, microneedle layer 38, with or without the thin metal seed film 34, is released from the secondary mould 30. The released structure is the desired microneedle array product 40, as shown in FIG. 10A, with an array of the desired microneedles 42. For simplicity only a single microneedle array is shown in FIG. 10A, although fabrication would normally involve an array of many such arrays being formed (for instance 64 (8×8) arrays, using the master mould of FIG. 4). FIG. 10B is an enlarged view of one of the frusto-pyramidal microneedles 42. The microneedles are shown here as being hollow. However, they can be solid if desired, if the metal or other material is deposited to a sufficient thickness.

The released secondary mould 30 can be reused or disposed after the release.

Figure 11:
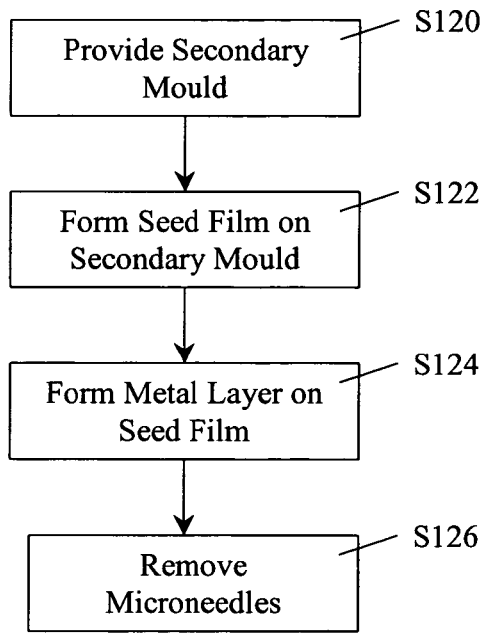
FIG. 11 is a flowchart relating to the manufacture of microneedles.

A flowchart describing the steps involved in making the microneedles according to this embodiment is shown in FIG. 11. At step S120 a secondary mould is provided. At step S122 a thin electrically conductive seed film is formed on top of the secondary mould and on the through-hole walls. A metal layer is electroformed onto the seed layer on top of the secondary mould and in the through-holes, in step S124. The microneedles are released from the secondary mould at step S126.

Alternative Geometries

The sizes and geometries of the final microneedles 42 on the microneedle array product 40 can be adjusted by changing the wire-cutting route 18 in making the master mould. With the cutting line 18 shown in FIG. 2 (repeated in the Y direction), the four side surfaces of the master mould needles 14 (and therefore the final microneedles 42) have the same shape, the same inclination angles with respect to the bottom surface, and a square cross section. By changing the uphill and downhill cut angles $\alpha$, $\beta$ of the cutting route, the master mould needle shape can be adjusted. Such master moulds of different geometries can be used to form secondary moulds of different geometries in the same manner as is described above. These secondary moulds of different geometries can be used to make microneedle array products, again in the same manner as mentioned above.

Figure 12:
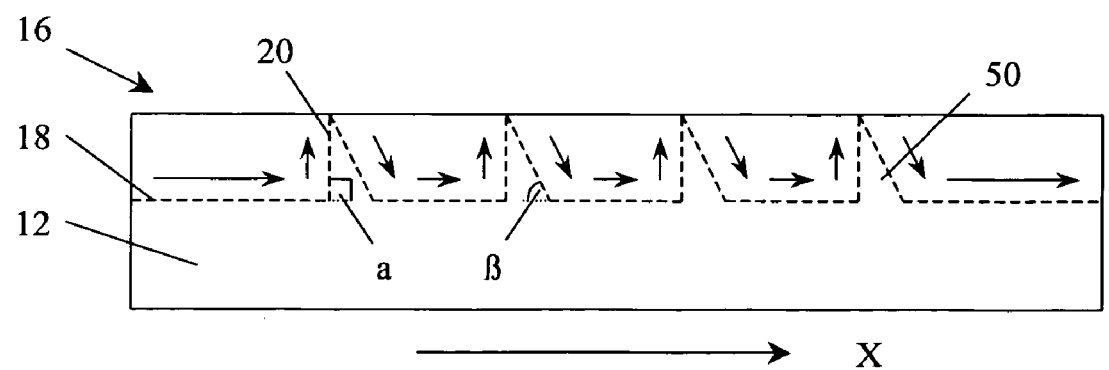
FIG. 12 is a side view of a plate to be cut into a master mould, showing an alternative path a wire takes during one wire cutting pass.

FIG. 12 is a side view of a parallelepiped tool steel plate 16 with mirror finished surfaces, similar to FIG. 2, to be cut into a master mould, showing the path a wire takes during one wire cutting pass for a first alternative shape of master mould needles 50.

Figure 13A:
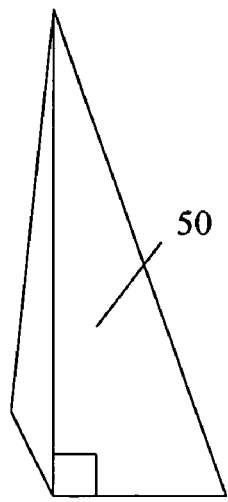
FIGS. 13A to 13D are enlarged views of alternative shapes of four-sided master mould needles.

FIG. 13A is an enlarged view of a first alternative shape of master mould needle 50. In this case the upward cut angle $\alpha=90$ degrees, whilst the downward cut angle $\beta<90$ degrees, in the X direction, whilst the upward and downward cut angles in the Y direction are unchanged from the first embodiment.

Figure 13B:
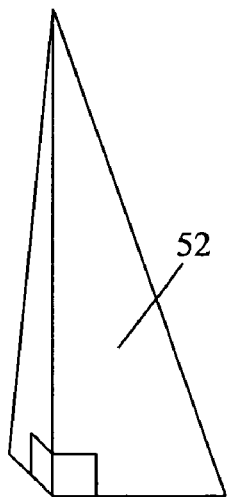

FIG. 13B is an enlarged view of a second alternative shape of master mould needle 52, where the upward cut angle $\alpha=90$ degrees, and the downward cut angle $\beta<90$ degrees, in both the X and Y directions.

Figure 13C:
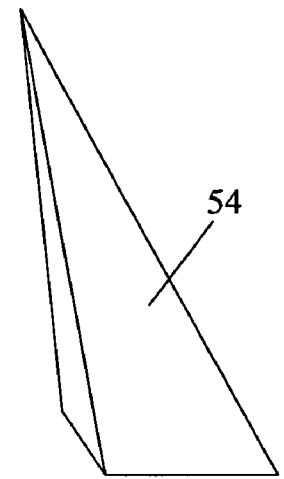

FIG. 13C is an enlarged view of a third alternative shape of master mould needle 54, where the upward cut angle $\alpha>90$ degrees, and the downward cut angle $\beta<180$ degrees– the upward cut angle $\alpha$, in the X direction, whilst the upward and downward cut angles in the Y direction are unchanged from the first embodiment.

Figure 13D:
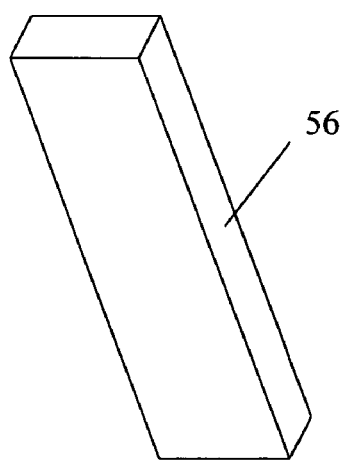

FIG. 13D is an enlarged view of a fourth alternative shape of master mould needle 56, where the upward cut angle $\alpha>90$ degrees, and the downward cut angle $\beta=180$ degrees– the upward cut angle $\alpha$, in the X direction, whilst the upward and downward cut angles in the Y direction are both at 90 degrees. This master mould needle 56 is a slanted parallelepiped needle.

Such varieties make the resistance of the microneedle penetration into the skin adjustable according to applications.

For slanted master mould needles, as in FIGS. 13C and 13D of the slanted microneedle with one side angle greater than 90 degrees, the pressing direction in making the secondary mould needs to be likewise slanted to facilitate the penetration of the master mould through the embossing plate to form the required shape of the opening.

In the embodiment of FIG. 13D, the top of the master mould needle 56 is not a single point. This means that where the cutting process reaches the top of the plate in the upward cut, it is no angled down immediately again but moves forwards a little along the top of the plate 16 first. This also may happen where two faces of the master mould needle meet at the top of the plate 16 or where the upward and downward cut angles $\alpha,\beta$ are so steep that the sides of the master mould needle would meet above the surface level of the plate 16.

In the above-described embodiments, the master mould needles and the ultimately produced microneedles have quadrilateral cross-sections arising from a square base. By changing the number of wire cutting passes and/or the angle through which the plate 16 is turned between each cut, other shapes are produced.

For instance, master mould needles having quadrilateral cross-sections arising from a parallelogram base can be derived by using only two wire cutting passes, where the angle through which the plate is turned between the first pass and second pass is not 90 degrees, for instance 60 degrees.

Figure 14A:
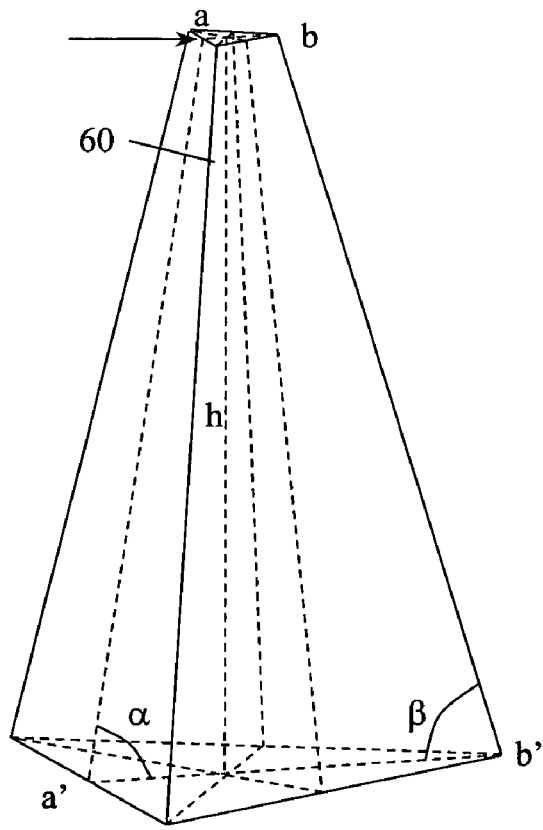
FIGS. 14A to 14I depict various aspects of a wire cutting process to fabricate a master mould with triangular pyramid master mould needles.

Master mould needles having triangular cross-sections arising from a triangular base can be derived by using three wire cutting passes. The triangular base can be equilateral if the angle through which the plate is turned between the first pass and second pass and between the second pass and the third pass is 120 degrees. Such a regular triangular master mould needle 60 is shown in FIG. 14A. In this case the upward cut angle $\alpha$ of a pair of upward and downward cuts defines one face of each needle but the downward cut angle $\beta$ of the pair of upward and downward cuts does not. The downward cut angle $\beta$ of each pair of cuts defines a plane containing the line joining the other two sides of the needle not defined by the upward cut of that pair. Once the angle of each surface of the master mould needle (which is the upward cut angle $\alpha$ in each pass in this embodiment) and the height of the master mould needle are decided, the downward position and cut angle $\beta$ can be determined precisely by mathematical calculation (even for non-regular triangles, although for non regular triangles formed by three cuts, the formed microneedles are not uniformly distributed on the base surface). The distance the wire passes through between finishing an upward cut and starting a downward cut is defined by the line "ab" of FIG. 14A. The distance between where the wire starts on its upward cut and where it finishes its downward cut is defined by the line "a'b'". The points "a" and "a'" are defined as the centre points of the top line and bottom line, respectively, of a first side (cut in the upward cut, the first cutting portion). The points "b" and "b'" are defined as the top and bottom, respectively, of the line joining the other two, adjacent faces. "h" is the vertical height of the master mould needle.

Various aspects of the wire cutting process for a master mould with regular triangular cross section master mould needles 60 are shown in FIGS. 14B to 14I.

Figure 14B:
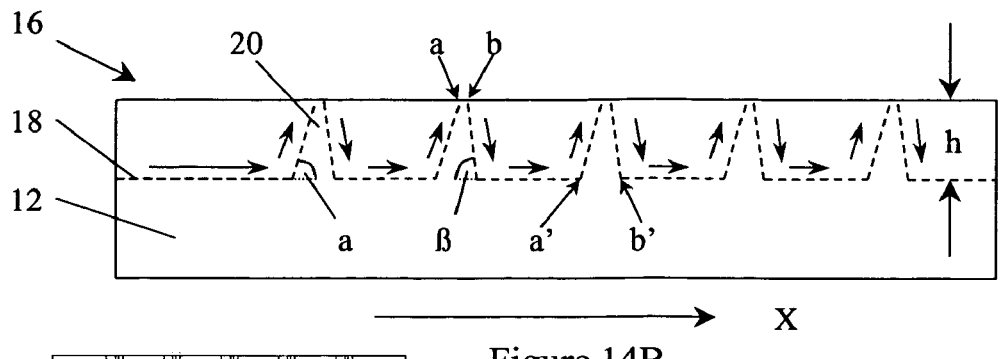

FIG. 14B is similar to FIGS. 2 and 12 and is a side view of a parallelepiped tool steel plate 16 with mirror finished surfaces, to be cut into a master mould, showing the path a wire takes during one wire cutting pass for regular triangular cross section master mould needles 60.

Figure 14C:
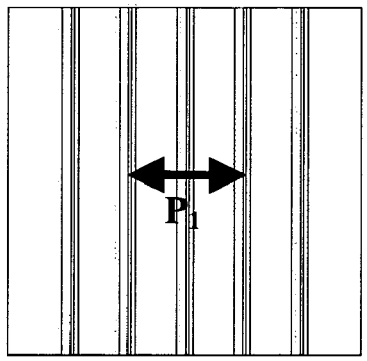
Figure 14D:
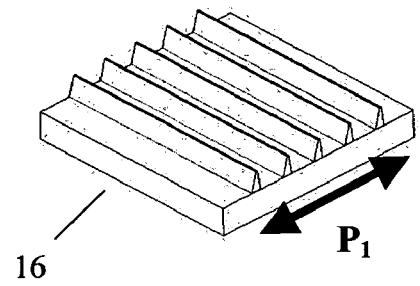

FIG. 14C is a top plan view of the steel plate 16 after a first pass P1. FIG. 14D is an isometric view of the same tool steel plate 16 of FIG. 14C.

Figure 14E:
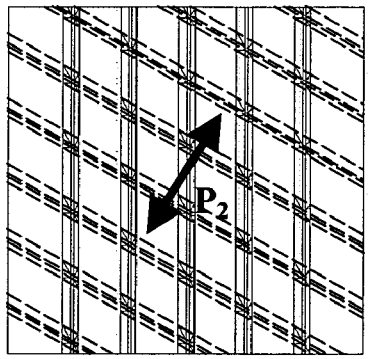
Figure 14F:
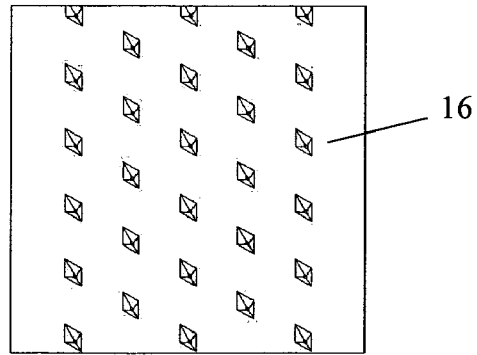

FIG. 14E is a top plan view of the steel plate 16 after a second pass P2. FIG. 14F is an isometric view of the same tool steel plate 16 of FIG. 14E.

Figure 14G:
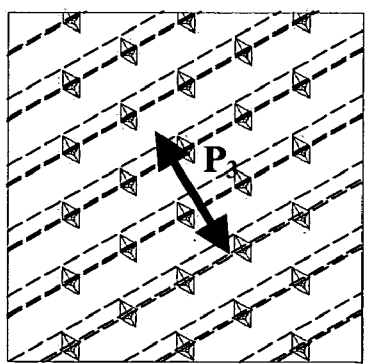
Figure 14H:
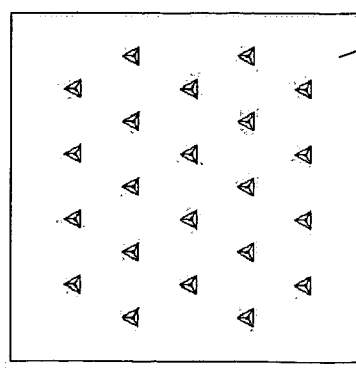
Figure 14I:
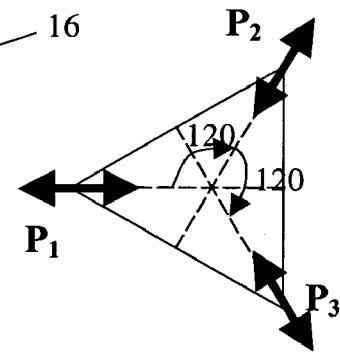

FIG. 14G is a top plan view of the steel plate 16 after a third pass P3. FIG. 14H is an isometric view of the same tool steel plate 16 of FIG. 14G. FIG. 14I is a cross-section through the regular triangular master mould needle 60 (at any point), showing the relationship between the three passes P1, P2, P3 and their relative angles.

The regular triangular master mould needle 60 of FIG. 14A can also be obtained by rotating the plate through 60 degrees between each pass. In this case, the upward cuts of the first and third passes define two of the faces of each master mould needle, whilst the downward cuts of the second pass define one of the surfaces of each master mould needle, with the upward cuts during the second cutting pass defining the planes containing the lines joining the other two faces. Alternatively, it could be the downward cuts of the first and third passes which define two surfaces of each master mould needle, whilst the upward cuts of the first and third passes define the planes containing the lines joining the other two faces.

When cutting master mould needles having triangular cross-sections arising from a triangular base, only one cut of each pair of upward and downward cuts in any pass defines any of the outer surfaces of the master mould needles. The other cut of each pair is at the angle that is required to cut the plane that contains the edge joining the two sides not being cut in that pair of cuts, or it may be shallower. This is to avoid the downward cut cutting away any material that might, otherwise be exposed during the cutting of either of the other passes. Otherwise this results in the production of other polygons: quadrilaterals, pentagons or hexagons, depending on how many cuts are steeper than the angle defining the plane joining the other two sides of the pyramid.

Figures 15A, 15B, 15C, 15D:
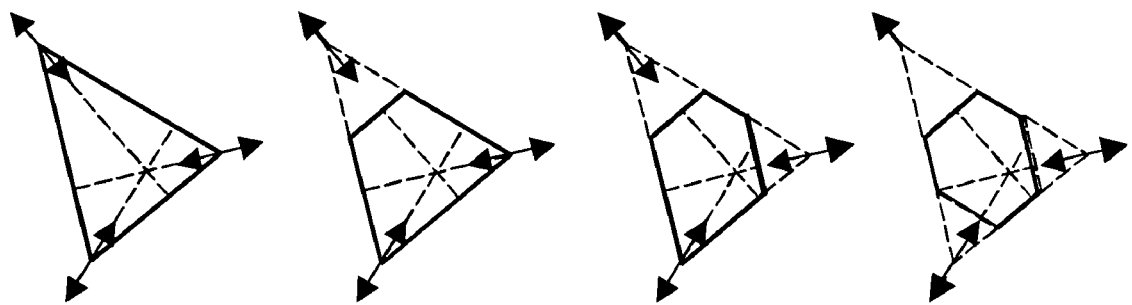
FIG. 15A to 15D depicts geometric variations (cross sections) of a mould needle through three wire cut passes.

The cross sections of mould needles for these variations are shown in FIG. 15A to 15D. FIG. 15A shows (by double arrows) three wire cut passes for a master mould with irregular triangle cross section. In each wire cut, the projection of the direction of movement of the wire on the base plane is parallel to the projection, on the base plane, of one height of the triangle (the projection of the perpendicular line from one vertex to its opposite side of the triangle, that opposite side being the side being cut). FIG. 15B shows a quadrilateral cross section, with one pair of parallel sides (ladder-shaped), of a mould needle formed by three wire cuts, one of which produces the two parallel sides. FIG. 15C shows a pentagonal cross section, with two pairs of parallel sides, of a mould needle formed by three wire cuts, two of which produce the two pairs of parallel sides. FIG. 15D is an irregular hexagonal cross section of a mould needle. Each side of the cross section is parallel to the opposite side. It is formed by three wire cuts, each of which produces one pair of the parallel sides.

For a mould needle with an hexagonal cross section, if the upward and downward cuts are made at the same angles in each of three passes, each at 120 degrees to each other (or 60 degrees as appropriate), a regular hexagonal master mould needle is produced. The process is shown in FIGS. 16A to 16H.

Figure 16A:
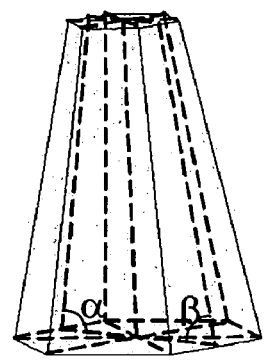
FIGS. 16A to 16H depict various aspects of three wire cut passes used to fabricate a master mould with hexagonal pyramid master mould needles.
Figure 16B:
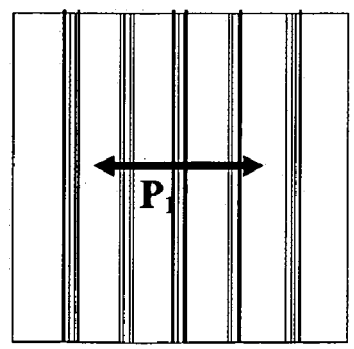
Figure 16C:
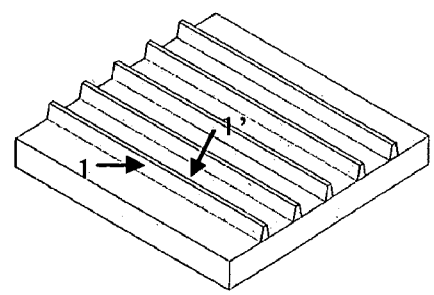
Figure 16D:
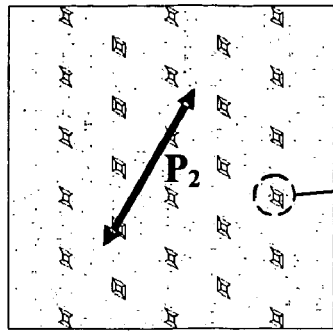
Figure 16E:
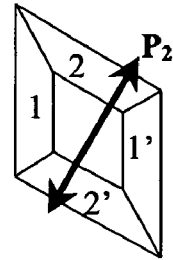
Figure 16F:
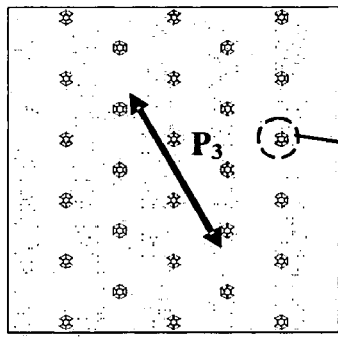
Figure 16G:
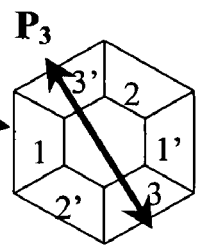
Figure 16H:
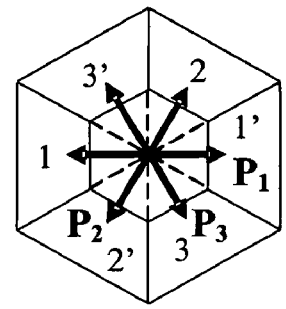

FIG. 16A is an enlarged view of a regular hexagonal master mould needle 62. FIG. 16B is a top plan view of a steel plate 16 after a first pass P1. FIG. 16C is an isometric view of the same tool steel plate 16 of FIG. 16B, where the surfaces that become faces 1 and 1' of the final microneedles are exposed. FIG. 16D is a top plan view of the steel plate 16 after a second pass P2. FIG. 16E is an enlarged view of a partially formed (rhomboidal) master mould needle within FIG. 16D, with surfaces that become faces 1, 1', 2 and 2' of the final microneedles exposed. FIG. 16F is a top plan view of the steel plate 16 after a third pass P3. FIG. 16G is an enlarged view of a fully formed master mould needle 62 within FIG. 16F, with final faces 1, 1', 2, 2', 3 and 3'. FIG. 16H is a cross-section through the regular hexagonal master mould needle 62 (at any point), showing the relationship between the three passes P1, P2, P3.

Similarly, it is possible to use four cutting passes, at 45 degree intervals, to produce master mould needles with a regular octagonal cross section. The cutting process is shown in FIGS. 17A to 17J.

Figure 17A:
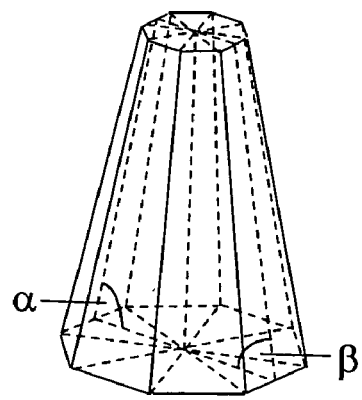
FIGS. 17A to 17J depict various aspects of four wire cut passes used to fabricate a master mould with octagonal pyramid master mould needles.
Figure 17B:
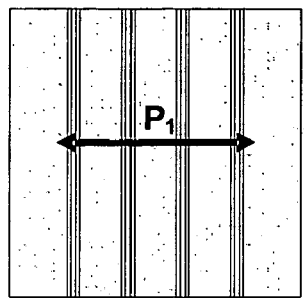
Figure 17C:
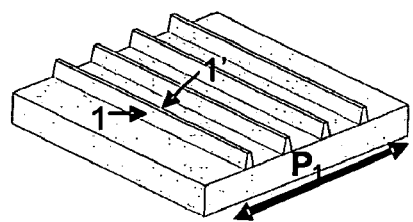
Figure 17D:
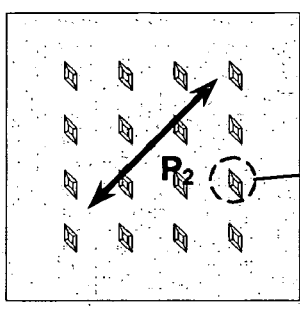
Figure 17E:
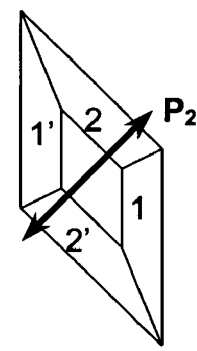
Figure 17F:
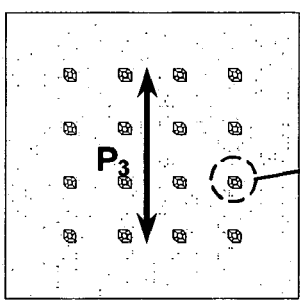
Figure 17G:
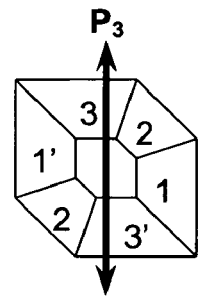
Figure 17H:
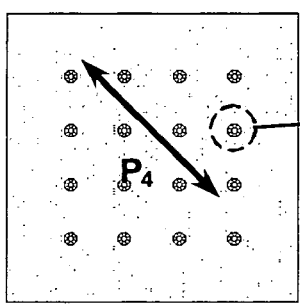
Figure 17I:
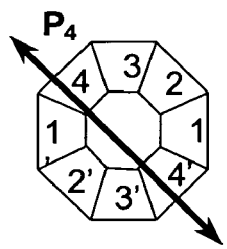
Figure 17J:
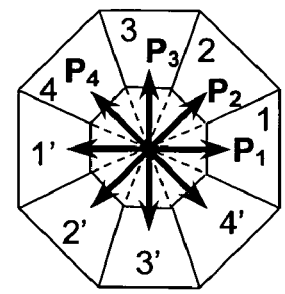

FIG. 17A is an enlarged view of a regular octagonal master mould needle 64. FIG. 17B is a top plan view of a steel plate 16 after a first pass P1. FIG. 17C is an isometric view of the same tool steel plate 16 of FIG. 17B, where the surfaces that become faces 1 and 1' of the final microneedles are exposed. FIG. 17D is a top plan view of the steel plate 16 after a second pass P2. FIG. 17E is an enlarged view of a partially formed (rhomboidal) master mould needle within FIG. 17D, with surfaces that become faces 1, 1', 2 and 2' of the final microneedles exposed. FIG. 17F is a top plan view of the steel plate 16 after a third pass P3. FIG. 17G is an enlarged view of a partially formed (irregular hexagonal) master mould needle within FIG. 17F, with surfaces that become faces 1, 1', 2, 2', 3 and 3' of the final microneedles exposed. FIG. 17H is a top plan view of the steel plate 16 after a fourth pass P4. FIG. 17I is an enlarged view of a fully formed (octagonal) master mould needle 64 within FIG. 17H, with final faces 1, 1', 2, 2', 3, 3', 4 and 4'. FIG. 17J is a cross-section through the regular octagonal master mould needle 64 (at any point), showing the relationship between the four passes P1, P2, P3, P4.

It is also possible to form mould needle arrays with regular polygonal cross-section of some even higher numbers of sides. It is a mathematical (geometry) problem to decide what side numbers can be formed by limited numbers of wire cuts across the whole plate.

The design of the master mould and in particular that of the master mould needles is determined from the design of the desired microneedles through mathematical calculations.

As with the master mould needles with square cross sections, the inclinations of the side surfaces of the triangular master mould needles can also be adjusted by adjusting the upward and downward cut angles α, β. When the upward cut angle α=90 degrees, one side surface of the master mould needles becomes normal to the bottom plane. When the downward cut angle β=90 degrees, the corresponding intersection line between two side surfaces becomes normal to the bottom surface. Other variations are also possible by changing the inclination angles. The same applies to master mould needles of other shapes.

Alternative Methods of Fabricating the Secondary Mould

One alternative way of fabricating the secondary mould is through electro-discharge machining (EDM). A master mould is made as described above, the master mould needles forming an array of EDM electrodes. The geometries and dimensions of the electrode array are based on those of the desired microneedles. A metal/alloy plate, for instance made of stainless steel, aluminium/aluminium alloy or nickel/nickel alloy, is placed below the EDM electrode array. EDM is conducted to make openings in the plate corresponding to the shapes and dimensions of the electrode array. Subsequently, the plate with the openings is coated with an insulating layer. The insulating layer is coated onto the bottom surface and all side surfaces, but not usually on the top surface (the one formed in contact with the master mould base surface). This plate can be used as a secondary mould, in the same way as the embossed plate mentioned earlier is. Microneedle arrays are fabricated by electroforming, as before. The secondary mould made in this way by EDM is a permanent one that can be reused again after release of the electroformed microneedle arrays. One advantage this metal secondary mould has over the polymer one made through embossing is that it is longer lasting.

Figure 18:
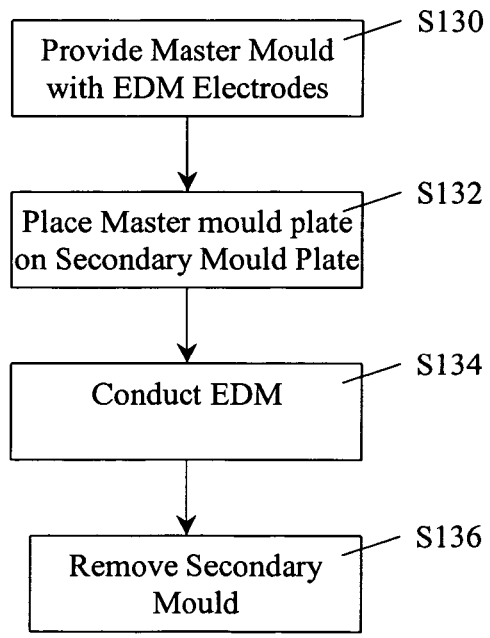
FIG. 18 is a flowchart relating to the manufacture of an alternative secondary mould according to a further exemplary embodiment.

A flowchart describing the steps involved in making the secondary mould according to this embodiment is shown in FIG. 18. At step S130 a master mould forming an array of EDM electrodes is provided. At step S132 a secondary mould plate is placed below the master mould. EDM is conducted at step S134 to form through-holes through the secondary mould plate. The secondary mould is removed from the master mould at step S136.

In another process for making the secondary mould, it is moulded onto the master mould, for instance by injection moulding. The master mould provides a first wall of the injection mould cavity, with the master mould needles extending into the cavity towards an opposing second wall. The secondary mould is moulded into the cavity between the first, master mould surface and the second, opposing wall. The second wall of the cavity can typically be one of two structures. In the first structure, this wall is simply a flat wall. In this case, the master mould needle height is equal to the final needle height. The mould cavity width when it is closed in the injection moulding operation is also equal to the final microneedle height. The master mould needles may extend part way or substantially all the way to the second wall. In the second structure, a plurality of receiving holes (or recesses) are provided on the second wall. The receiving holes are at positions which correspond to all the master mould needles on the first, master mould wall. The height of the needles is larger than the final needle height. The mould cavity width, when it closes during the injection moulding operation, is again equal to the final microneedle height. The depth of the holes is equal to or slightly larger than the difference between the master mould needle height and the cavity width. The cross section of each hole (or recess) is just enough (in size and shape) to contain the cross section of the master mould needle at the height of the final needle height (i.e. at the second wall surface).

The secondary mould is fabricated by injection moulding a polymer material, such as (but not limited to) polycarbonate, PMMA, nylon or silicon rubber. When silicon rubber is used, the 'injection' process is conducted at room temperature and the solidification is by adding in curing agent into the pre silicon rubber liquid (cold casting process).

Another alternative for making the secondary mould is by electroforming a proper metal such as (but not limited to) Ni, Ni—Fe alloy onto the master mould (fabricated as described earlier). Proper release measure may be needed before electroforming. This may take the form of depositing a thin electrically conductive layer (preferably between about 100 to about 1000 nm), which does not have high adhesion to the master mould, on the master mould surface. The non-high adhesion to the master mould is so that the thin electrically conductive layer does not form a strong bond with the master mould. This electrically conductive layer may, for instance be formed of aluminium, titanium or chromium. The thickness of the plated metal/alloy may be larger than the final microneedle height. After release, the backside surface of the electroformed piece (the side not in contact with the master mould needles during the electroforming) is ground/milled to a thickness equal to the final needle height. An electrical insulation layer is then applied to the back surface and all side surfaces, but not usually on the front surface (the one formed in contact with the master mould base surface) and not on the hole walls. The electroformed piece is usable as permanent secondary mould for making microneedles.

Figure 19A:
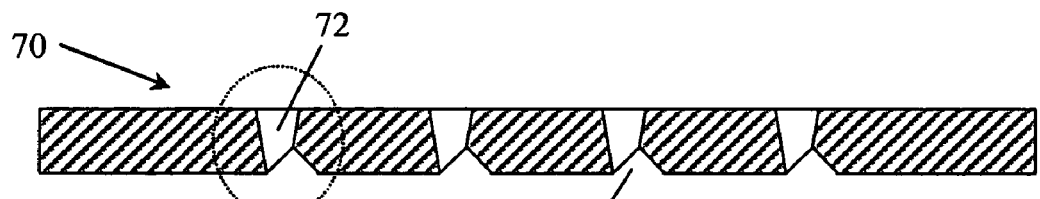
FIG. 19A is a cross section through a portion of a modified secondary mould.
Figure 19B:
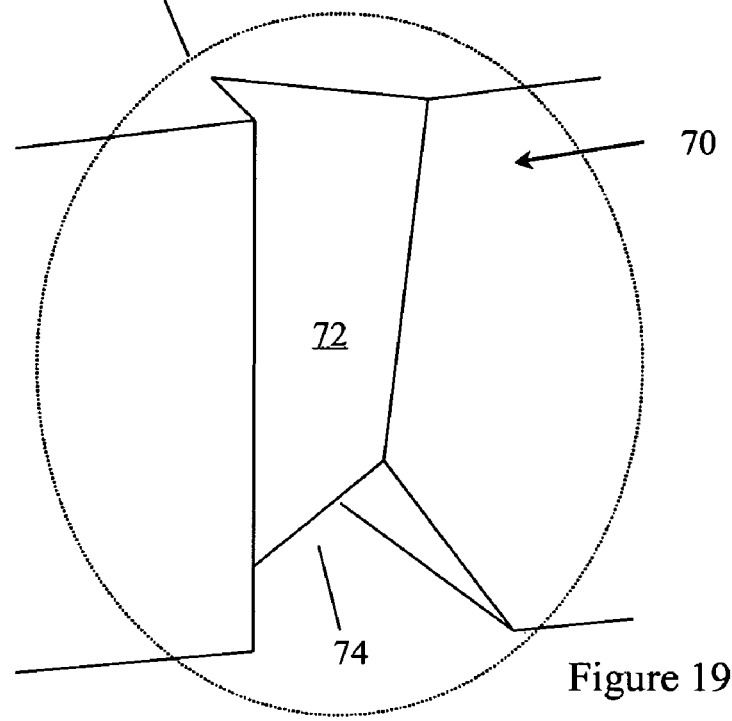
FIG. 19B is an enlarged view of an opening in the modified secondary mould of FIG. 17A.

A modification to the secondary mould, however it is made, is shown in FIGS. 19A and 19B. FIG. 19A is a cross section through a portion of a modified secondary mould 70; showing modified triangular pyramid frustum through-holes 72. FIG. 19B is an enlarged isometric view of one such through-hole 72.

V-shaped grooves 74 are formed in the bottom surface of the modified secondary mould 72, as it appears in FIG. 19A. The bottom surface of the modified secondary mould 70 for this purpose is the surface with the smaller openings to the through-holes 72. The V-shaped grooves 74 run parallel to the lines of through-holes 72. Each through-hole 72 meets at least one surface or edge of a V-shaped groove 74. Normally one of the two intersection lines between each V-shaped groove 74 and the bottom surface of the modified secondary mould 72 is aligned with and meets one of the edges of each of the smaller openings to the through-holes 72 in one line of through-holes 72. Each V-shaped groove 74 extends upwards into the through-holes 72, the edge of which they are aligned with and meet. In the embodiment of FIG. 19A, the tip of the V-shaped groove 74 meets an inner surface of each through-hole 72 in the line. The inner surface that the V meets is on the other side of the through-holes 72 from the edge that the V-shaped groove 74 meets at the bottom surface.

Figure 19C:
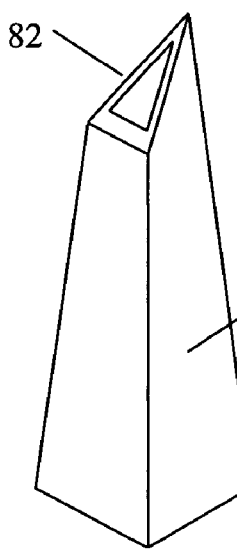
FIGS. 19C to 19E is an enlarged view of a triangular microneedle made from the modified secondary mould of FIG. 19A.

The purpose of the grooves 74 is to increase the sharpness of the microneedles fabricated from the secondary mould 70. It does this by making a slanted cut across the through-holes 72 that are used to form the microneedles, with the ends of the microneedles taking the cut shapes. FIG. 19C is an enlarged view of a triangular microneedle 80, with a sharp tip 82, made from the modified secondary mould of FIG. 19A.

Figure 19D:
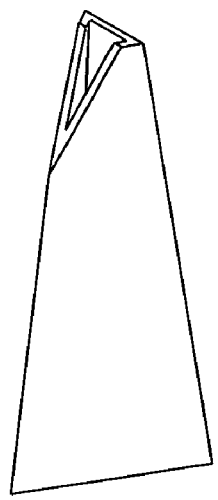
Figure 19E:
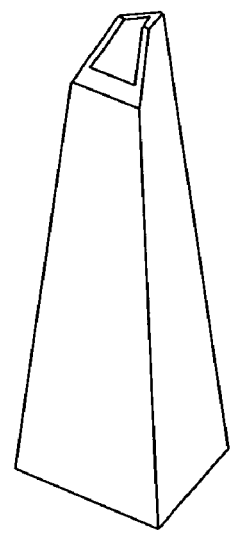

Such grooves can be used for other shaped microneedles, as well as the triangular ones. The groove cross section need not be V-shaped but may take other shapes, for instance semicircular, the chord of a circle, parabolic, etc. Individual grooves, in cross-section, have a first groove surface extending from the second surface of the secondary mould to a deepest point of the groove within the secondary mould. The first groove surface may extend completely across the width of the through-holes the groove intercepts to form a single slope across the tip of the microneedles (FIG. 19C). Normally the grooves intercept over half the width of each through-hole (FIGS. 19D and 19E). The first groove surface may extend only partially across the width of the through-holes the groove intercepts, with a second surface of the groove intercepting the rest of each such hole, to form two sharp tips on different sides of the microneedles.

The grooves can be moulded into the plates that are formed into the secondary moulds or machined or burned into the plates, for instance by cutting, laser ablation or milling or may be formed in the plates in any other suitable way. Where the secondary mould is formed by moulding onto the master mould, as mentioned above, ridges in the opposing surface of the mould could be provided form the grooves directly during the moulding process. Where the secondary mould is formed by EDM or electroforming, the grooves are preferably made first, before the insulation layer application. Then the electrical insulation layer is applied to the secondary mould back surface and all side surfaces (including the groove surface). If the grooves are not made before the insulation layer has been applied, a second electrical insulation layer application for the groove surface is needed.

Alternative Use of Secondary Mould Earlier, microneedle arrays are described as being formed through electroforming on the secondary mould. As one possible alternative, the secondary mould whether produced as described with reference to FIGS. 5A and 5B, whether produced as described elsewhere (for instance by EDM or electroforming) or produced in another manner, can be used as one wall of a mould, with through-holes corresponding to the mould needles of the master mould and with or without tip needle sharpening grooves. Moulding, for instance injection moulding, onto the same face of the secondary mould as the metal is formed onto in FIGS. 9A and 9B, followed by a release produces the microneedle array. This method can be used to create solid needles, for instance of a polymer material such as a polycarbonate, PMMA, nylon, etc. If the face opposing the secondary mould has protrusions corresponding in position to the through-holes in the secondary mould, and extending to the same level as the tops of the through-holes in the secondary mould, but being narrower, the moulded microneedles can be hollow.

The embodiments of the invention allow the easy production of strong and ductile hollow microneedle arrays or solid needles, such as solid polymer needles, on a large industrial scale. Moulds for fabricating microneedles can be made using cheap polymeric materials so the moulds can be of low cost and disposable. Moreover the exemplary method of making the secondary (microneedle) mould is cheaper using the wire cutting method to make the master mould. The use of the wire cutting method allows easy variation in the size and shape of the microneedles, whether regular or irregular, tapered or non-tapered, straight or slanted or of various numbers of sides. The sharpness of such microneedles can be further enhanced by the use of grooves in the back of the secondary mould. This allows the easy production of sharp microneedles, which makes them better at penetrating the skin and delivering the liquid into the subject. Such microneedle arrays can be used in painless injection devices to replace conventional injection needles/syringe.

The invention claimed is:

1. A method of manufacturing a master mould for use in making microneedles, from a block of a first material, the method comprising:
    cutting across the block in at least two cutting passes in different directions to provide a master mould comprising a master mould base surface with a plurality of master mould needles protruding therefrom, wherein in each cutting pass at least one surface of each of the plurality of protruding master mould needles are formed;
    wherein the master mould needles correspond to the microneedles to be made.

2. A method according to claim 1, wherein cutting across the block comprises wire cutting across the block.

3. A method according to claim 1, wherein cutting across the block in at least two different directions comprises a cut in each direction.

4. A method according to claim 3, wherein individual cuts comprise:
    a plurality of base cutting portions, cutting the master mould base surface;
    a plurality of first sloped cutting portions, cutting from the base cutting portions to the tips of the master mould needles; and
    a plurality of second sloped cutting portions, cutting from the tips of the master mould needles to the base cutting portions; and wherein individual base cutting portions are separated by a pair of a first sloped cutting portion and a second sloped cutting portion; and at least one of each pair of first and second sloped cutting portions cuts a surface of a plurality of master mould needles.

5. A method according to claim 1, wherein the master mould needles are triangular pyramid shaped; and the master mould base surface with a plurality of master mould needles protruding therefrom are provided by three cuts in three different directions.

6. A method according to claim 4, wherein only one of each pair of first and second sloped cutting portions cuts a surface of a plurality of master mould needles.

7. A method according to claim 6, wherein the other of each pair of first and second sloped cutting portions cuts an edge of a plurality of master mould needles.

8. A method according to claim 1, wherein the master mould needles are hexagonal; and the master mould base surface with a plurality of master mould needles protruding therefrom are provided by three cuts in three different directions.

9. A method according to claim 1, wherein the master mould needles are square pyramid shaped; and the master mould base surface with a plurality of master mould needles protruding therefrom are provided by two cuts in two different directions.

10. A method according to claim 9, wherein the two cuts are at right angles to each other.

11. A method according to claim 1, wherein the master mould needles are octagonal; and the master mould base surface with a plurality of master mould needles protruding therefrom are provided by four cuts in four different directions.

12. A method according to claim 11, wherein the four cuts are at 45 degrees to each other.

13. A method according to claim 4, wherein both of each pair of first and second sloped cutting portions cuts a surface of a plurality of master mould needles.

14. A method according to claim 5, wherein the three cuts are at 60 or 120 degrees to each other.

15. A method according to claim 1, further comprising coating the master mould base surface and the master mould needles with a hard coating.

16. A method according to claim 15, wherein the hard coating comprises a coating of one or more of: a diamond carbon coating, a diamond like carbon coating, an electroless Ni coating, a hard chrome coating, a nitride coating, a carbide coating and a boride coating.

17. A method according to claim 1 further comprising: applying a thin electrically conductive layer on the master mould surface, as a release layer.

18. A method according to claim 17, wherein the release layer comprises a coating of one or more of: an aluminium coating, a titanium coating, a chromium coating, a carbon coating and a diamond like carbon coating.

19. A method of manufacturing a secondary mould for use in making microneedles, comprising:

providing a master mould for use in making microneedles from a block of a first material by cutting across the block in at least two cutting passes in different directions to provide a master mould comprising a master mould base surface with a plurality of master mould needles protruding therefrom, wherein in each cutting pass at least one surface of each of the plurality of protruding master mould needles is formed and wherein the master mould needles correspond to the microneedles to be made;

forming, on the master mould, a secondary mould such that the secondary mould has formed on a first surface of the secondary mould, in contact with the master mould base surface during forming the secondary mould, the holes corresponding to the master mould needles and extending from the first surface, to an opposing, second surface of the secondary mould; and removing the secondary mould from the master mould.

20. A method according to claim 19, wherein forming the secondary mould comprises hot embossing, electro-discharge machining, electroforming or injection moulding the secondary mould against the master mould.

21. A method according to claim 19, further comprising applying an electrical insulation coating to the surfaces of the secondary mould.

22. A method according to claim 21, wherein the electrical insulation coating is applied to the sides and second surface of the secondary mould.

23. A method according to claim 19, wherein the second surface of the secondary mould comprises a plurality of grooves extending into the secondary mould, which grooves intercept the holes near the second surface.

24. A method according to claim 23, wherein individual grooves, in cross-section, have a first groove surface extending from the second surface of the secondary mould to a deepest point of the groove within the secondary mould, which first groove surface extends at least part way across the width of holes the groove intercepts.

25. A method according to claim 23, wherein the grooves intercept over half the entire widths of the holes.

26. A method according to claim 23, wherein the grooves intercept the second surface at or close to the edges of the holes at the second surface.

27. A method according to claim 23, further comprising providing said plurality of grooves.

28. A method according to claim 20, wherein forming the secondary mould comprises injection moulding the secondary mould within the cavity of a secondary mould injection mould.

29. A method according to claim 28, wherein the secondary mould injection mould is a mould for a secondary mould with the master mould base surface forming a first surface of the cavity and the master mould needles extending into the cavity towards a second, opposing surface of the cavity.

30. A method according to claim 29, wherein the ridges form said grooves in the second surface of the secondary mould.

31. A method according claim 28, wherein forming the secondary mould comprises injection moulding a polymer into the secondary mould injection mould.

* * * * *